(12) United States Patent
Ross et al.

(10) Patent No.: US 6,672,996 B2
(45) Date of Patent: Jan. 6, 2004

(54) PELVIC FLOOR EXERCISE DEVICE

(76) Inventors: Anthony C. Ross, P.O. Box 1149, Johns Island, SC (US) 29457; Peter A. Guagliano, 370 Bay Ridge Pkwy., Brooklyn, NY (US) 11209

( * ) Notice: Subject to any disclaimer, the term of this patent is extended or adjusted under 35 U.S.C. 154(b) by 22 days.

(21) Appl. No.: 10/167,714

(22) Filed: Jun. 12, 2002

(65) Prior Publication Data

US 2002/0169056 A1 Nov. 14, 2002

Related U.S. Application Data

(63) Continuation-in-part of application No. 09/459,798, filed on Dec. 12, 1999, now Pat. No. 6,406,411.

(51) Int. Cl.$^7$ .............................................. A63B 21/02
(52) U.S. Cl. ........................ 482/121; 482/91; 600/591; 73/379.01
(58) Field of Search .................. 482/121, 122, 482/126, 128; 600/546, 561, 591; 33/12; 73/379.01

(56) References Cited

U.S. PATENT DOCUMENTS

| | | | | |
|---|---|---|---|---|
| 4,016,867 A | * | 4/1977 | King et al. | 128/2 |
| 4,121,572 A | * | 10/1978 | Krzeminski | 128/2 |
| 4,224,951 A | * | 9/1980 | Hasson et al. | 128/2 |
| 5,483,832 A | * | 1/1996 | Pauser et al. | |

* cited by examiner

Primary Examiner—Jerome W. Donnelly
(74) Attorney, Agent, or Firm—Loren G. Helreich; Browning Bushman

(57) ABSTRACT

An improved apparatus is disclosed for use in diagnosing and treating pelvic floor musculature disorders. The device includes a head (10) mounted on a shaft (12), with a barrier (14) mounted on the shaft (12) between the handle (18) and head (10). An indicator (16) may be mounted on the shaft (12). The apparatus may provide magnetic resistance to pelvic floor musculature contraction to (1) measure and track the progress of pelvic floor musculature strength, and (2) exercise pelvic floor musculature to improve strength at a private, patient-determined frequency. Alternative embodiments are either spring biasing members or the biasing property of a stretched elastomeric material.

12 Claims, 3 Drawing Sheets

PELVIC FLOOR EXERCISE DEVICE

RELATED CASE

The present application is a continuation-in-part of U.S. Ser. No. 09/459,798 filed Dec. 12, 1999 for PELVIC FLOOR EXERCISE DEVICE now U.S. Pat. No. 6,406,411.

FIELD OF THE INVENTION

This invention relates generally to pelvic floor exercises, and more specifically to devices and methods that can quantify pelvic floor diagnostic findings and monitor and improve pelvic floor strength.

BACKGROUND OF THE INVENTION

Disorders of pelvic support are a significant health care concern, resulting in the loss of billions of dollars annually. Associated with the rigors of childbirth, trauma, and the aging process, these disorders not only result in financial loss, but have a profound emotional component often altering one's self image as well. The resultant loss in function and self-esteem associated with such disorders is often extremely debilitating, leading to prolapse, discomfort, and both urinary and sexual dysfunction.

To combat these disorders, a variety of therapeutic approaches have been entertained. Both non-surgical and surgical techniques have been utilized with varying degrees of success. While surgical management certainly has its role, it is not without risk and expense. Medical management likewise must be carefully individualized, requiring thorough surveillance by the prescribing physician.

With this in mind, non-operative therapies to enhance the support of pelvic tissues are highly desirable. Traditionally, supportive devices such as the pessary or specialized pelvic floor exercises, commonly referred to as Kegel exercises, have been the mainstay of therapy. While pessaries provide artificial support to pelvic floor musculature, Kegel exercises help strengthen such tissues. Patients are trained to utilize isometric contractions of the pubococcygeus and levator ani muscles to strengthen the pelvic floor musculature and thus improve function. Utilization of such exercises requires training and motivation, and variations of such methodology have been successfully utilized and proven with respect to the ability to overcome stress incontinence.

Several investigators have confirmed the benefits of such non-operative therapies, both subjectively and objectively. Two studies by Henalla, et al, published in the British Journal of Obstetric and Gynecology in 1988 and 1989, demonstrated improvement in two-thirds of patients utilizing such closely monitored therapy. The later study showed such exercises to be even more beneficial than both electrical stimulation of the pelvic floor and estrogen supplementation. Studies such as that of Tchou, et al, published in the 1988 Journal of Physical Therapy confirmed such outcomes utilizing urodynamic evaluations, both prior to and after pelvic floor exercise therapy. In a variation of this theme, Peattie, et al, published in the British Journal of Obstetric and Gynecology in 1988, utilized weighted vaginal cones to provide resistance with which pelvic muscle contraction could be taught, musculature strengthened, and function restored.

Critical to the success of such therapy is an understanding of how best to perform these exercises correctly, considering that when proper technique is not utilized, the potential for a worsening of function also exists. In one study by Bump, et al, published in the American Journal of Obstetric and Gynecology in 1991, less than half of those given either verbal or written instructions were able to illicit an ideal Kegel effort as demonstrated by an increase in the force of urethral closure.

With these principles and concepts in mind, it is clear that non-operative means are proven to be successful in improving the function of the pelvic floor. Such techniques may be learned and, as such, the ability to perform them properly is critical to achieving the outcome desired. It is these aforementioned concepts which have spawned desire to improve upon the non-operative techniques that have traditionally been utilized to improve pelvic floor function and further alleviate the need for both medical and surgical therapies.

The prior art demonstrates electronic and pneumatic pelvic floor exercise devices, e.g., Sawchuck U.S. Pat. No. 5,733,230 and Sample U.S. Pat. No. 5,674,238, spring-biased exercise devices, e.g., Wallick U.S. Pat. No. 5,865,715, heated and vibrating mechanism exercise devices, e.g., Benderev U.S. Pat. No. 5,782,745, and exercise devices utilized external to the body, e.g., Harris U.S. Pat. No. 5,531,226. However, the prior art poses the threat of further injury to the patient attributed to malfunction of the electronic, thermal, vibrating or pneumatic. Additionally, the complexity of the prior art diminishes reliability, in that numerous moving parts introduce a higher likelihood for malfunction. Finally, the prior art requires multiple apparatus for the performing both the diagnosis and treatment of pelvic floor injuries.

In order for pelvic floor disorders to be properly and efficiently diagnosed, it is highly desirable to provide a non-operative method for both physician and patient diagnosis, as well as a hygienic and reliable diagnostic tool that is easy to use in private, as an alternative to traditional procedures which can be inaccurate, cumbersome and embarrassing. In order for pelvic floor disorders to be properly and efficiently treated, it is highly desirable to provide a method and device allowing patients to perform exercise treatment in private, with self-governed frequency, in a simple and hygienic manner, and in any environment.

The disadvantage of the prior art are overcome by the present invention, and an improved pelvic floor exercise device and methods for pelvic floor musculature dysfunction diagnosis and treatment is hereafter disclosed.

SUMMARY OF THE INVENTION

The present invention provides a device for diagnosing and treating pelvic floor dysfunction which, in one embodiment, combines both the traditional approach of Kegel exercises and an innovation utilizing attractive magnets. This technique allows for several advantages over the existing technology, in that magnets may be calibrated so as to allow the patient to more properly learn the techniques associated with successful treatment. Further, the patient may follow personal progress, objectively demonstrating improvements in the strength of one's pelvic floor musculature. This invention offers advantages over the prior art in that performing exercise with the device is not postural based, since the magnets may be calibrated so that exercises may be performed in a reproducible and progressive manner regardless of body habitus and positioning. This invention also offers patient safety and the anti-microbial benefits of magnet associated therapies, benefits not offered by prior art.

The magnetic attraction between a magnetic head and barrier may provide a biasing feature against which the contracting pelvic floor musculature may react. The head and barrier may be so magnetized as to provide a constant and reproducible attractive force between the head and the barrier, a force which may be calibrated via magnet and material selection. The head may be secured by thread engagement to a metal shaft. The shaft may have a measuring indication along a portion of a length of the shaft, may pass through the approximate center of the barrier. The head may have a generally semi-spherical shaped upper end and a generally conical lower end. The barrier may have a generally hourglass shaped barrier as to provide proper placement of the device in relation to the patient's body. The lower end of the shaft may be secured by thread engagement to a handle to prevent the separation of the barrier from the shaft. The contraction of the pelvic floor musculature may move the head away from the stationary barrier, such that the shaft may slide upwards through the barrier. As the shaft slides through the barrier, an indicator opposite the barrier from the head may slide down the shaft, indicating the degree to which the head has traveled from its initial position when the pelvic floor musculature was at rest. This indication feature is a primary objective of this invention. The feature allows the physician and patient to measure the strength of the pelvic floor musculature.

The magnetic head may be detachable from the device shaft in such a manner that it may be reattached to a pin. The pin may provide an attach point for a lanyard to the magnetic head. Once the head is detached from the device and reattached to the lanyard, the patient may repeat the above pelvic floor musculature contraction procedure using only the head and lanyard, as opposed to the entire device. In this manner, the patient may continue to exercise the pelvic floor musculature in a private, self-paced manner, thereby increasing the strength of the pelvic floor musculature.

In another embodiment, magnets are mounted on plates, and are configured to repel each other and thus the attraction of the plates. Movement of the bulb away from the plate which serves as the barrier is thus resisted by the magnets.

In yet another embodiment, a flexible elastomeric member may be slid over the bulb and held in position against a single plate by a screw cap. Movement of the bulb away from the plate is resisted by the elastomeric member, which is stretched during use of the pelvic floor exercise device.

It is an object of this invention to provide a pelvic floor exercising device comprising a shaft, a measuring indication along a portion of a length of the shaft, a head secured to an upper end of the shaft, and a barrier moveably mounted on the shaft. It is a related object to provide such a device that provides hygienic, safe, reproducible and private diagnosis and rehabilitation.

It is a feature of the present invention that the device may provide a combination of magnetically attractive head and barrier components on a mutual shaft having a measuring indication. The barrier may have a substantially hourglass shaped configuration. It is a further feature that the barrier and the indicator may slide along a portion of the length of the shaft. Magnets may also be mounted on a pair of plates, with the magnets configured to repel each other. It is a further feature that the head may be detached from the shaft and thereafter attached to a pin and lanyard.

Yet another embodiment of the invention uses the elastomeric properties of a generally tubular closed end elastomeric member for resisting movement of the bulb or head away from a base plate. This embodiment also has advantages due to easy lubrication, ease of keeping the device clean, and a device wherein both the distance (stroke length) and force required to move that stroke length are easily variable.

It is an advantage of the present invention that the pelvic floor exercise device is relatively simple in design and construction, and is highly reliable. It is an additional advantage that magnets offer an advantage over the aforementioned utilization of weighted vaginal cones in strengthening the pelvic musculature, in that performing such exercise is no longer postural based. Regardless of both body habitus and positioning, magnets may be calibrated so that exercises may be performed in a reproducible and progressive manner. In this way, outcomes and process can be prospectively followed by the physician and patient alike.

It is a further advantage of the present invention that magnet associated therapies have an anti-microbial benefit shown in other venues, and that such therapy may provide improvements not only in function, but in the vaginal milieu as well. This advantageous feature is particularly of interest in the perimenopausal and postmenopausal population in which both of these disorders are more prominent.

It is a further advantage that an alternative to medical and/or surgical therapies with respect to the dilemma of pelvic floor dysfunction is provided by the apparatus, which may significantly improve upon an already existing non-surgical modality, and which has been proven and desired.

These and further objects, features and advantages of the present invention will become apparent from the following detailed description, wherein references are made to the figures in the accompanying drawings.

DETAILED DESCRIPTION OF THE PREFERRED EMBODIMENT

Figure 1:
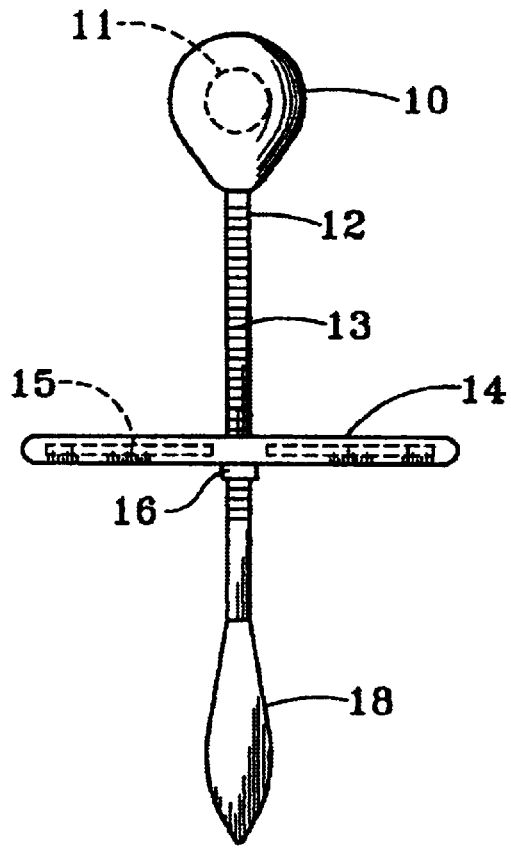
FIG. 1 is a simplified side view of a preferred embodiment of the invention, illustrating a handle and detachable head connected by a shaft, with a barrier and indicator located adjacent one another on the shaft.
Figure 2:
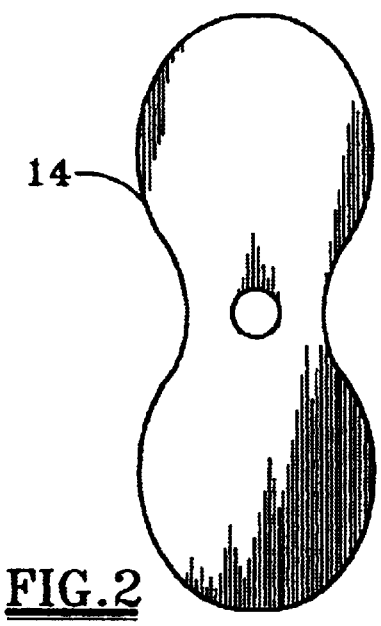
FIG. 2 is a simplified top view of the barrier shown in FIG. 1, illustrating the hourglass shape of the barrier.
Figure 3:
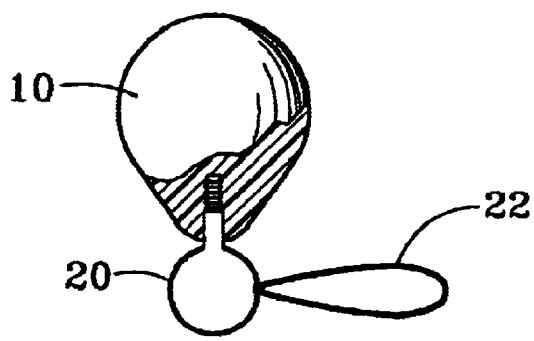
FIG. 3 is a simplified side view of another embodiment of the invention, illustrating a detachable head assembled to a pin having an attached lanyard.
Figure 4:
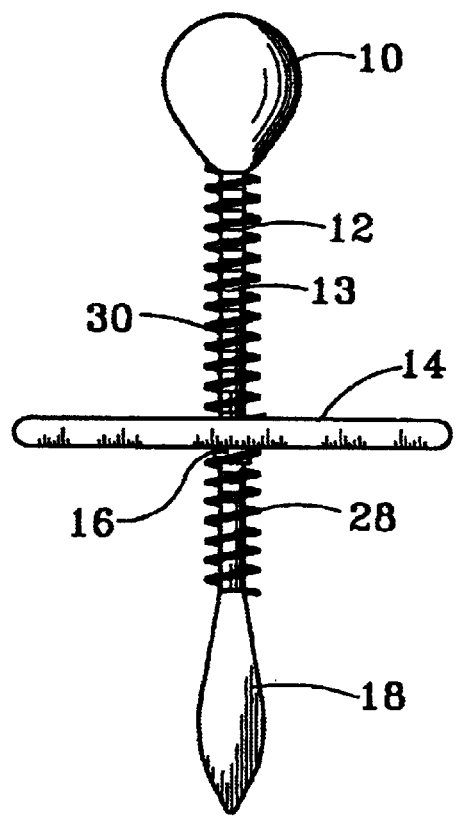
FIG. 4 is a simplified side view of another embodiment of the invention, illustrating a handle and detachable head connected by a shaft, a barrier and indicator located adjacent one another on the shaft, and biasing members between head and the barrier and between the barrier and the handle.

Reference is made to the attached drawings only for the purpose of demonstrating preferred embodiments and not for the purpose of limiting the same. FIG. 1 illustrates generally a pelvic floor exercise device in the configuration used primarily for diagnosis. The device is held by the handle 18 and placed into the injured tissue, such that the barrier 14 rests against the exterior surface of the treatment area with the long axis of the barrier 14 parallel to the patient's front-to-back direction. FIG. 3 illustrates generally a second configuration used primarily for exercise treatment. In this configuration, the shaft 12 is removed from the head 10 and replaced with the pin 20, to which a lanyard 22 is secured. FIG. 4 illustrates generally another embodiment of the invention, in which biasing members 28 and 30 each oppose the separation of the head from the barrier.

In the FIG. 1 embodiment, a handle 18 is secured to a lower end of a shaft 12. The handle 18 may be spatulated in a manner similar to a reflex hammer. A head 10 is secured to an upper end of the shaft 12. In a preferred embodiment, the head has a generally semispherical shaped upper end and a generally conical shaped or half-egg shaped lower end. A preferred embodiment depicts a barrier 14 as moveably mounted on the shaft 12 between the head 10 and the handle 18. An indicator 16 is mounted on the shaft 12 between the barrier 14 and the handle 18, and is moveably responsive to the separation of the head 10 from the barrier 14. In a preferred embodiment, the head 10 and barrier 14 are composed of and/or house a magnetic material, providing a magnetically attractive force to one another, opposing the separation of the head from the barrier. The magnetic material may have any desired configuration, and in the head 10 has a generally ball-shaped configuration, while in the barrier 14 comprises a pair of elongate strips. The magnetic material 11 and the strips 15 are shown in dashed lines in FIG. 1. Each of the magnetic materials may thus be embedded in a suitable plastic material. In a preferred embodiment, the barrier 14 has a generally hourglass shaped configuration to conform to the exterior genitalia of the user, and is relatively flat. The head and a portion of the shaft are thus inserted into the vagina to the extent permitted by the attraction of the barrier, with the relatively flat upper surface of the barrier resting against an exterior surface of the user surrounding her vagina. In a preferred embodiment, the shaft 12 has measuring indications 13 along a portion of a length of the shaft. In the FIG. 3 embodiment, a head 10 similarly has a generally semi-spherical shaped upper end and a generally conical shaped lower end is secured to a lanyard 22.

In the FIG. 4 embodiment, a handle 18 is secured to a lower end of a shaft 12. A head 10 is secured to an upper end of the shaft 12. The head has a generally semi-spherical shaped upper end and a generally conical shaped lower end. The FIG. 4 embodiment depicts a barrier 14 as moveably mounted on the shaft 12 between the head 10 and the handle 18. An indicator 16 is mounted on the shaft 12 between the barrier 14 and the handle 18, and is moveably responsive to the separation of the head 10 from the barrier 14. In the FIG. 4 embodiment, biasing members 28 and 30 are moveably mounted on the shaft 12 between the head 10 and the barrier 14 and between the barrier 14 and the handle 18. The barrier 14 has a generally hourglass shaped configuration. In a preferred embodiment, the shaft 12 has a measuring indication along a portion of a length of the shaft.

In the preferred embodiments, the head 10 is approximately 3 centimeters in height and 2.5 centimeters in diameter. In the preferred embodiments, the barrier 14 is approximately 3 centimeters wide and 7 centimeters long. In the preferred embodiments, the handle 18 is 7.5 centimeters in height, and the handle 18 attached to the shaft 12 is approximately 14 centimeters in height. The preferred embodiments depict the shaft 12 as having a substantially cylindrical cross-section, but the shaft 12 cross-sectional shape may take the form of other geometric shapes. The preferred embodiment depict the barrier 14 and indicator 16 as each having an internal aperture with a generally circular cross-section, such that the barrier 14 and indicator 16 may slide along the length of the shaft 12, but other embodiments may have cross-sectional shapes of other geometric forms.

In a preferred embodiments, the handle 18 is attached to the shaft 12 by threaded engagement, although other embodiments may utilize other methods for attaching the handle 18 to the shaft 12, such as welding, adhesive, or by fabricating the handle 18 and shaft 12 as a single component. In the preferred embodiments, the head 10 is also attached to the shaft 12 by thread engagement, although other embodiments may utilize other forms of attachment. In the preferred embodiments, the head 10 may be removably attachable and re-attachable to the shaft 12, such that a pin 20 may be attached to the head 10 in the same manner that the shaft 12 is attached to the head 10. In the FIG. 3 embodiment, the pin 20 is mounted to the head 10 by the same means utilized to mount the shaft 12 to the head 10, although other forms of attachment are possible. A lanyard 22 composed of nylon twine is secured to the head 10, although other embodiments may depict the lanyard 22 secured to the pin 20. Other embodiments may depict the lanyard 22 as composed of other materials.

The preferred embodiments depict the head 10 and the handle 18 secured to the shaft 12 by thread engagement, but other forms of engagement are possible. A preferred embodiment depicts springs as biasing members 28 and 30 between the head 10 and the barrier 14 and between the barrier 14 and the handle 18, but other embodiments may include fewer or additional springs. When in use, the coil spring 30 is thus in tension, while the coil spring 28 is in compression. Only one coil spring may be necessary to achieve the desired results. Preferred embodiments depict a handle 18 secured to the shaft 12, although other embodiment may replace the handle 18 with a stop to prevent separation of the barrier 14 from the shaft 12, or may completely eliminate the handle 18, so as to allow the separation of the barrier 14 from the shaft 12. In the preferred embodiments the shaft 12 is composed of metal, but other materials may be used in other embodiments. In the preferred embodiments the head 10 and the barrier 14 are composed of hard plastic, but other materials may be used in other embodiments.

A process for diagnosing pelvic floor injury of injured musculature comprising providing a shaft 12, a portion of a length of the shaft 12 having a measuring indication, mounting a removeably attachable and re-attachable head 10 on an upper end of the shaft 12, mounting a moveable barrier 14 on the shaft 12 between a lower end of the shaft 12 and the head 10, and mounting a moveable indicator 16 on the shaft 12 between a lower end of the shaft 12 and the barrier 14. The indicator 16 is moveably responsive to separation of the head 10 from the barrier 14. In the FIG. 1 embodiment, magnetic materials 11 and 15 may act as biasing members to oppose separation of the head from the barrier. In the FIG. 4 embodiment, biasing members 28 and 30 are provided each for opposing separation of the head 10 from the barrier 14. The head 10 is placed into the injured musculature and thereafter the injured musculature is contracted, such that the pelvic floor musculature exerts an upward force against the head 10. Other embodiments may further comprise detaching the head 10 from the shaft 12 and re-attaching the head 10 to a lanyard 22, thereafter proceeding with the pelvic floor musculature contraction described above. Other embodiments may further comprise examining the displacement of the indicator 16 along the shaft 12 after the contraction of the pelvic floor musculature. Other embodiments may further comprise providing a handle 18 secured to the lower end of the shaft 12.

The magnetic biasing members as disclosed herein are preferred. The coil spring biasing members, while functionally satisfactory, present additional contamination concerns. The spring biasing member could be provided within rather than being external of the shaft 12.

Other biasing members may be used, such as pneumatic or hydraulic cylinders. Other embodiments considered within the scope of this invention may include components constructed from a variety of materials, including resinous compounds, other non-metallic compounds, metallic compounds, special alloys, or any combination thereof.

Figure 5:
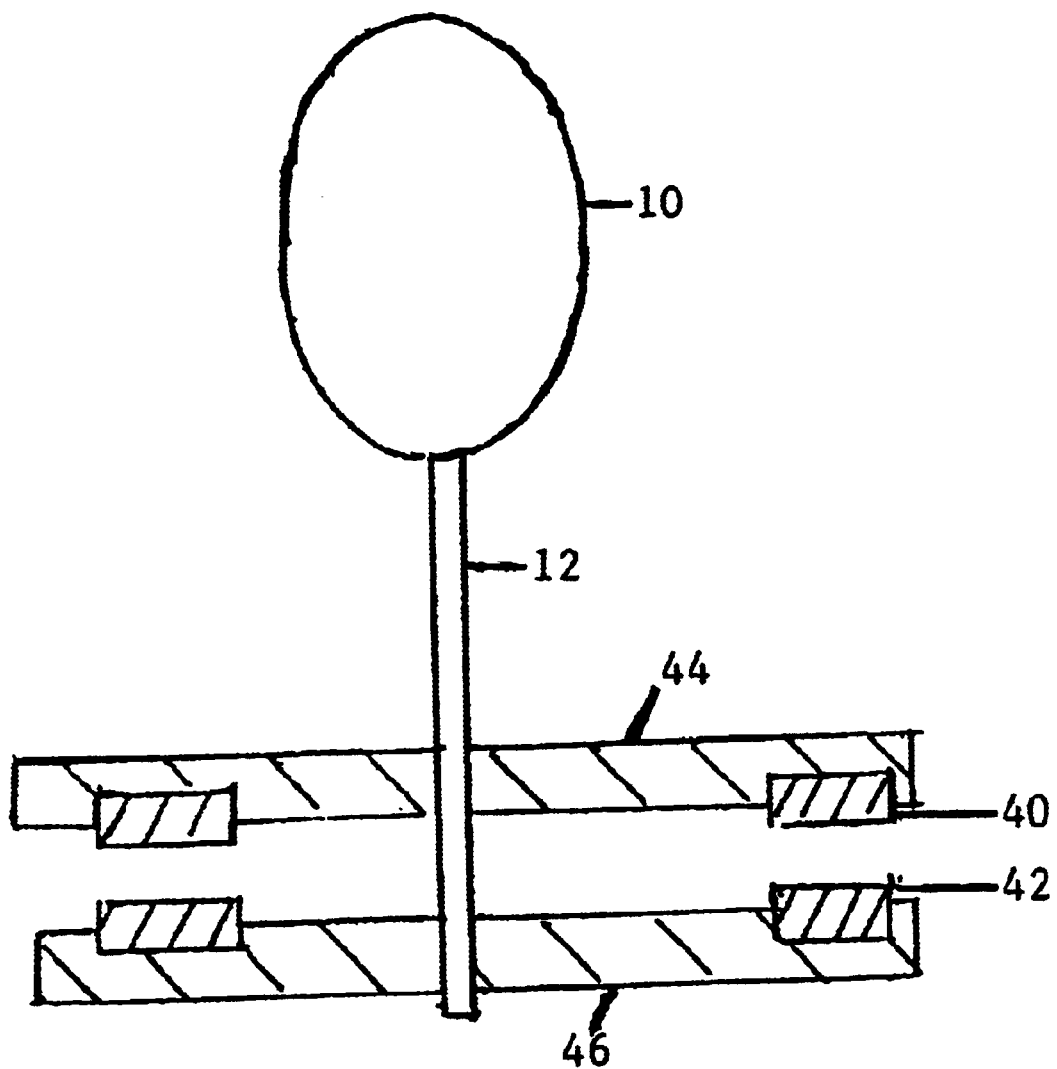
FIG. 5 is a side view of an alternate embodiment of the invention.

FIG. 5 depicts another embodiment of the invention, wherein the bulb or head 10 is provided at the end of shaft 12. Magnets 40, 42 are mounted on plates 44, 46, and are configured to repel each other and thus the attraction of the plates. Plate 44 may thus be similar to barrier 14. Movement of the bulb 10 away from the plate 44 is resisted by the magnets. Shaft 12 may be threaded or otherwise secured to the plate 46, which may have any desired configuration, including a profile similar to plate 44. The shaft 12 passes axially through and is movable relative to plate 44. The shaft 12 also serves as a guide to the plate 44, and the plate 44 a guide to the shaft, and a bearing on the plate may be used, if desired.

Figure 6:
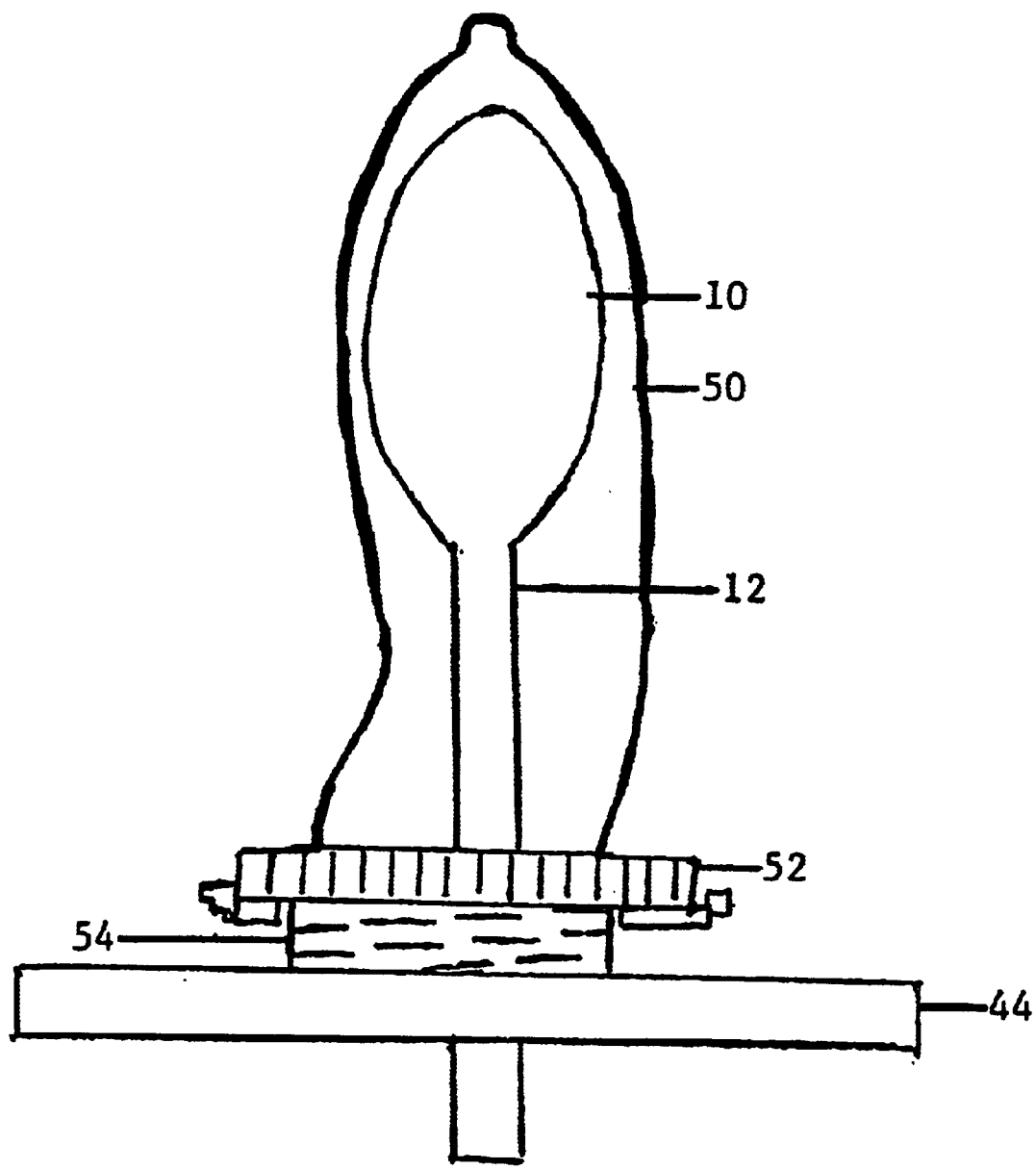
FIG. 6 is a side view of yet another embodiment of the invention.

FIG. 6 discloses a further embodiment where the bulb 10 and shaft 12 pass through a single base plate 44. The flexible elastomeric member 50, generally having a configuration and properties similar to a condom, may be slid over the bulb and held in position by a screw cap 52, which is threaded to a fitting 54 adhered to the base plate 44. The generally tubular closed end elastomeric member 50 may be placed over the threaded fitting 54, and a screw cap 52 tightened to hold the base of the elastomeric member in place. In another embodiment, a female component rather than a male component may be fixed to the base plate 44, and a male threaded component, such as a ring, then may be threaded to the female component to hold the elastomeric member in place. The screw cap 52 may include finger tabs 56 to assist in manual tightening and loosening of the cap 52 from the plate. This embodiment has advantages since lubrication may be easily provided in the condom-like device, and the exercise device is easy to clean, since the condom is disposable. Moreover, the distance of bulb movement by the user and the strength required for that movement may be easily varied by varying the dimensions and properties of the condom. Also, the fitting 54 may be threaded to the base plate 44, and fittings of different axial length may be provided so that the user changes the position of the base of the condom by selecting a different axial length fitting, thereby varying both the stroke and the strength required for movement of the bulb.

The foregoing and the following disclosure and description of the pelvic floor exercise device and methods are illustrative and explanatory thereof. This invention is not intended to be limited to the illustrated and discussed embodiments, as one skilled in the art will appreciate that various changes in the size, shape and materials, as well as in the details of the construction or combination of features of the pelvic floor exercise device may be made without departing from the spirit of the invention.

What is claimed is:

1. A pelvic floor exercise device, the device comprising:
   a shaft;
   a head secured to an upper end of the shaft;
   a base plate moveably mounted on the shaft, the barrier having a relatively flat upper surface for resting against an exterior surface of the user surrounding her vagina; and
   an elastomeric biasing member being generally tubular and having an open end and a closed end, and;
   wherein said elastomeric biasing member is configured to be positioned over said head and at least a portion of said shaft, and said open end of said elastomeric member is removably secured to said base plate.

2. A device as defined in claim 1, further comprising:
   a threaded member for securing the elastomeric biasing member to the base plate.

3. A device as defined in claim 1, further comprising:
   a stop secured to a lower end of the shaft for preventing separation of the base plate from the shaft; and
   an indicator mounted on the shaft indicating separation of the head from the barrier.

4. A device as defined in claim 1, wherein the baseplate is generally hourglass shaped.

5. A device as defined in claim 1, further comprising:
   a handle secured to a lower end of the shaft.

6. A device as defined in claim 1, wherein the upper end of the head is generally semi-spherical in shape and the lower end of the head is generally conical in shape.

7. A method of diagnosing pelvic floor injury of injured musculature, comprising:
   providing a shaft;
   mounting a head on an upper end of the shaft;
   mounting a baseplate on the shaft;
   a elastomeric biasing member being generally tubular and having an open end and a closed end, and; wherein said elastomeric biasing member is configured to be positioned over said head and at least a portion of said shaft, and said open end of said elastomeric member is removably secured to said base plate;
   placing the head into the injured musculature; and
   thereafter contracting the injured musculature, such that the pelvic floor musculature exerts a force against the head to move the head away from the barrier.

8. A method as defined in claim 7, further comprising:
   mounting a moveable indicator on the shaft to indicate separation of the head from the base plate.

9. A method as defined in claim 7, further comprising:
   removably attaching and detaching the head from the upper end of the shaft.

10. A method as defined in claim 7, further comprising:
    removing the head from the shaft; and
    securing a lanyard to the head.

11. A method as defined in claim 7, further comprising:
    securing a handle to a lower end of the shaft.

12. A method as defined in claim 7, further comprising:
    securing a stop secured to a lower end of the shaft for preventing separation of the barrier from the shaft.

* * * * *

UNITED STATES PATENT AND TRADEMARK OFFICE
CERTIFICATE OF CORRECTION

PATENT NO.    : 6,672,996 B2
DATED         : January 6, 2004
INVENTOR(S)   : Anthony C. Ross et al.

It is certified that error appears in the above-identified patent and that said Letters Patent is hereby corrected as shown below:

<u>Column 8,</u>
Lines 1, 18 and 56, change "barrier" to -- base plate --.
Line 6, change "and;" to -- ; and --.
Line 32, change "a elastometric" to -- providing an elastrometric --.

Signed and Sealed this

Fourth Day of May, 2004

JON W. DUDAS
*Acting Director of the United States Patent and Trademark Office*